United States Patent [19]

Ikeda et al.

[11] Patent Number: 4,841,775
[45] Date of Patent: Jun. 27, 1989

[54] VIBRATORY TRANSDUCER

[75] Inventors: Kyoichi Ikeda; Tetsuya Watanabe; Yasushi Higashino, all of Tokyo, Japan

[73] Assignee: Yokogawa Electric Corporation, Tokyo, Japan

[21] Appl. No.: 145,156

[22] Filed: Jan. 19, 1988

Related U.S. Application Data

[62] Division of Ser. No. 899,519, Aug. 22, 1986, abandoned.

[30] Foreign Application Priority Data

Sep. 6, 1985 [JP] Japan .................... 60-192169

[51] Int. Cl.⁴ ........................................ G01L 11/00
[52] U.S. Cl. ........................................ 73/704; 310/324
[58] Field of Search ............ 73/704, 702; 310/324, 310/338, 321, 323

[56] References Cited

U.S. PATENT DOCUMENTS 4,229,979 10/1980 Greenwood ...................... 73/704

Primary Examiner—Donald O. Woodiel
Attorney, Agent, or Firm—Moonray Kojima

[57] ABSTRACT

A vibratory transducer comprising a vibratory beam composed of an n-type layer and having at least one end fixed. The vibratory beam is formed by selectively etching an n-type layer formed by adding impurities locally to a single silicon crystal. The vibratory transducer also comprises means for vibrating the vibratory beam and means for detecting vibration of the vibratory beam. The vibratory transducer measures pressure, temperature, density, etc, by detecting change in the resonant frequency of the vibratory beam. The vibratory beam can be finely etched irrespective of the density of the impurities therein by forming the vibratory beam in an alkaline aqueous solution while applying a negative DC or pulsed voltage to a p-type layer and a positive DC or pulsed voltage to an n-type layer. The vibrating and detecting means for the vibratory beam can be easily provided by making a diode and a transistor including the vibratory beam in the transducer.

24 Claims, 11 Drawing Sheets

VIBRATORY TRANSDUCER

This is a division of application Ser. No. 899,519, filed 8/22/86, now abandoned.

BACKGROUND OF THE INVENTION

1. Field of Invention

This invention relates to a vibratory transducer for detecting change in the frequency of vibration of a vibratory beam formed of a single silicon crystal due to a change in force of environment while vibrating the vibratory beam at its natural frequency.

2. Description of the Prior Art

Figure 1:
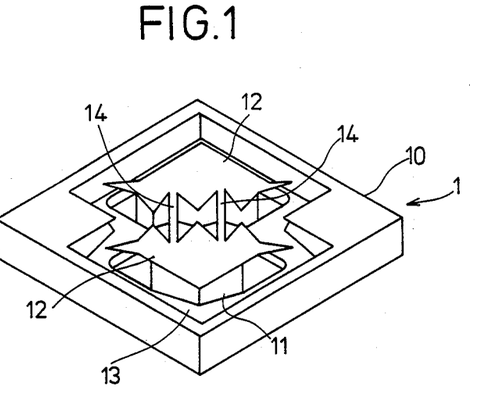
FIG. 1 is a perspective view depicting a conventional vibrating transducer.
Figure 2:
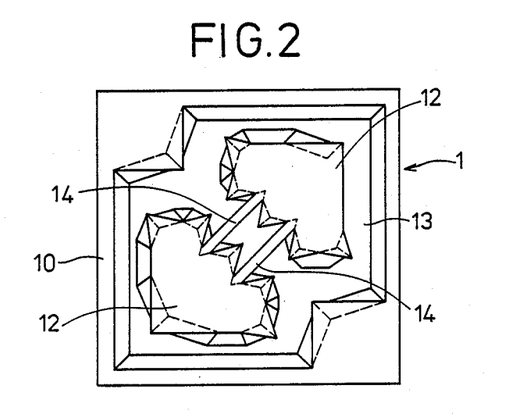
FIG. 2 is a plan view of the transducer of FIG. 1.
Figure 3:
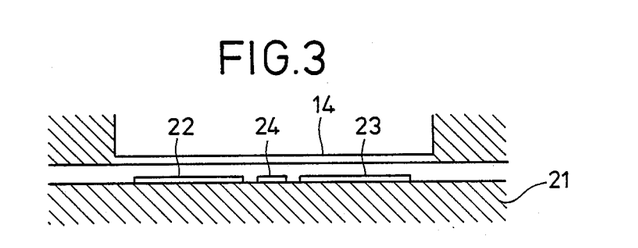
FIG. 3 is a fragmentary cross sectional view of the transducer of FIG. 1.

There is known a transducer which comprises vibratory beams formed of a semiconductor, such as disclosed in UK Patent Application SN 24,186 filed in 1978, and corresponding to Japan Laid-Open Patent Publication No. 55-26,487, and described in FIGS. 1,2,3. FIG. 1 is a perspective view of the conventional transducer and FIG. 2 is a plan view of the transducer.

In FIGS. 1,2,3, a silicon substrate 1 is doped locally with boron at a density of $4 \times 10^{19}$ atoms/cm$^3$ more in certain regions (two regions are left as projections 12 and two regions are left as vibratory beams 14), and is masked at portion which is left as a frame 10. Silicon substrate 1 is then anisotropically etched in an aqueous solution of catechol and diamine acid to form frame 10, projections 12, partition 13 and vibratory beams 14. Vibratory beams 14 are disposed on top of projections 12.

FIG. 3 shows a transducer portion in fragmentary cross section. Vibratory beams 14 are disposed in spaced relation to the bottom 21 of the transducer, on which there are disposed a transducer driver electrode 22, a pickup electrode 23, and a protective electrode 24. Where the transducer is used as a pressure sensor, an end or frame thereof is attached to a pressure source to be measured.

Since a p+ layer is formed in the silicon substrate 1 to a depth of 1 micrometer by impurities of boron at a density of $4 \times 10^{19}$ atoms/cm$^3$, the conventional vibratory transducer has the following disadvantages.

(1) Due to different diameters of the atoms of silicon and boron, a slip line is created by lattice defects, resulting in deterioration of mechanical and electrical properties of the crystal. Consequently, the transducer is subjected to large residual stresses and has a varied temperature coefficient. It is thus difficult to produce a transducer which is highly sensitive and reliable.

(2) Since the density of the impurities is of a limited value that can be injected, the following deficiencies occur (a) A pn-junction diode or transistor for detecting distortion cannot be formed in the transducer.

(b) A MOS-FET of a buffer cannot be formed in the transducer even if a piezoelectric film for vibrating the vibratory beams is electrodeposited.

(c) A piezoelectric resistor for detecting distortion of the vibratory beams cannot be formed in the transducer.

SUMMARY OF THE INVENTION

Accordingly, an object of the invention is to overcome the aforementioned and other deficiencies and disadvantages of the prior art.

Another object is to provide a vibratory transducer which is highly sensitive and reliable, simple in structure, and highly accurate.

The foregoing and other objects are attained by the invention which encompasses a vibratory transducer which comprises a vibratory beam composed of an n-type layer and having at least one end fixed, the vibratory beam being formed by selectively etching an n-type layer formed by adding impurities locally to a single silicon crystal. The vibratory transducer also includes means for vibrating the vibratory beam and means for detecting vibration of the vibratory beam. The vibratory transducer measures pressure, temperature, density, etc., by detecting change in the resonant frequency of the vibratory beam. The vibratory beam is formed in an alkaline aqueous solution while applying a negative DC or pulsed voltage to a p-type layer and a positive DC or pulsed voltage to an n-type layer.

DETAILED DESCRIPTION OF THE PREFERRED EMBODIMENTS

Turning now to FIGS. 4-7, which depicts a first illustrative embodiment of the invention, there is depicted a single silicon crystal 30 of the p-type containing impurities at a density of pb $10^{15}$ or $10^{17}$ atoms/cm$^3$ or less. A diaphragm 31 is formed by etching silicon substrate 30. An n+ diffused layer 32 is formed locally on the surface of diaphragm 31 by adding impurities at a density ranging from $10^{17}$ to atoms/cm$^3$. The p layer of diaphragm 31 is underetched except for a surface portion of n+ diffused layer 32, thus forming a vibratory beam 34 composed of an n+ layer. Vibratory beam 34 is disposed above a recess 35 and is supported at two spaced points. Piezoelectric elements (such as of ZnO) 36, 36a, are disposed near the supported points of vibratory beam 34, and are each in the form of a thin film having a thickness of about 1 micrometer. Electrodes 37,37a, serve to vibrate piezoelectric elements 36,36a, respectively, and are connected by leads (not shown) to an external circuit (not shown) in insulated relation to the p layer of diaphragm 31 and vibratory beam 34. An SiO$_2$ layer 38 having a thickness of about 4 micrometers is formed on diagrphram p layer 31 by chemical vapor deposition (CVD) and has an opening or space 33 above vibratory beam 34. A silicon cover 39 having a thickness of about 5 micrometers, for example, is made of the same material as diaphragm 31. Silicon cover 39 and SiO$_2$ layer 38 on diaphragm 31 are connected by anodic joining in vacuum to evacuate an area in which the vibratory beam is formed.

One illustrative example of the dimensions of vibratory beam 34 is as follows. Thickness h is 2 micrometers. Length L is 200 micrometers. Width d is 5 micrometers.

Figure 6:
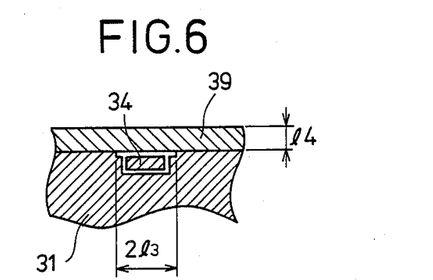
FIG. 6 is a cross sectional view taken along line X—X in FIG. 5.

The resistance to a static pressure on the area in which vibratory beam 34 is formed can be attained by suitably increasing the ratio $l_4/l_3$ of the width $2l_3$ of the hole shown in FIG. 6 and the thickness $l_4$ of silicon cover 39. For example, if $l_3=5$ micrometer $l_4=5$ micrometers, and the maximum stress $\sigma_{max}$ of silicon is 10 kg/mm$^2$, then pressure resistance $P_o$ is given by the following $$P_o = (l_4/l_3)^2 \cdot \sigma_{max} = 1000 \text{ kg/cm}^2$$

Figures 4, 5:
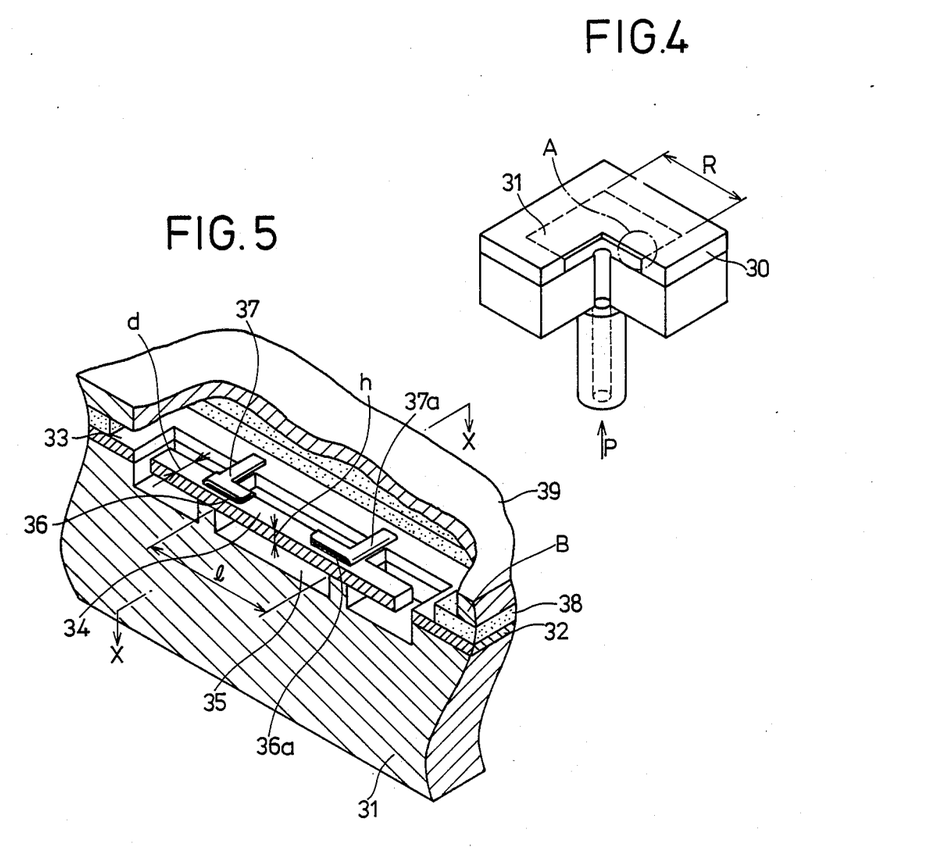
FIG. 4 is a perspective view depicting a first illustrative embodiment of the invention wherein the embodiment is used illustratively as a pressure sensor.
FIG. 5 is an enlarged perspective view, partly cut away, depicting a portion A of the embodiment of FIG. 4.

Any distortion of vibratory beam 34 due to in phase pressures applied axially thereto can be neglected by suitably reducing $l_3/R$ (wherein R is the length of one side of diaphragm 31 of FIG. 4). Vibratory beam 34 can be finely etched by photolithography.

Figure 7:
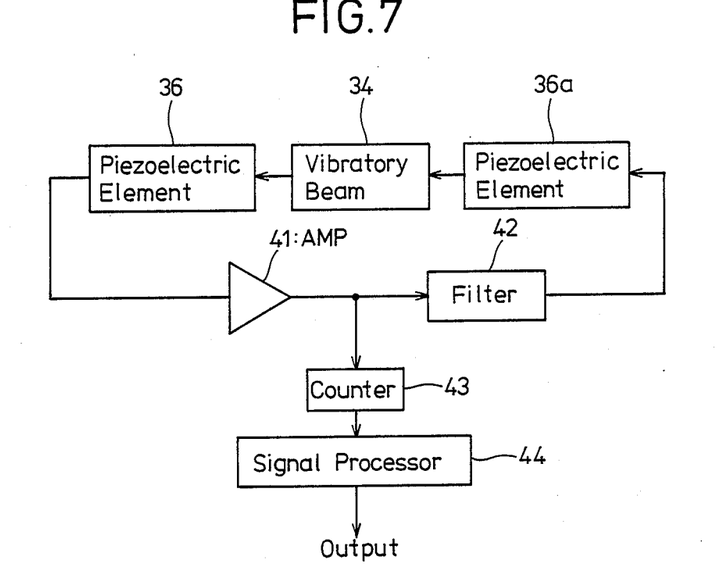
FIG. 7 is a block diagram depicting a circuit for vibrating a vibratory beam and for detecting vibration of the vibratory beam of the embodiment of FIG. 4.

FIG. 7 shows in block form a circuit for vibrating vibratory beam 34 and for detecting vibrations thereof. Vibratory beam 34 is vibrated by piezoelectric element 36a formed on one end thereof. The vibratory distortions of vibratory beam 34 are detected by piezoelectric element 36, which produces a signal. The signal from piezoelectric element 36 is amplified by an amplifier 41 and is fed back through a positive feed back loop via a filter 42 to piezoelectric element 36a to enable the circuit to be self oscillated at the natural frequency of vibratory beam 34. The output of amplifier 41 is counted by a counter 43 which generates a frequency signal which is then processed by a signal processor 44 and outputted as an output signal.

By fixing the vibratory transducer by fixing means (not shown) and applying a pressure to diaphragm 31 in the direction of arrow P in FIG. 4, diaphragm 31 is deformed to distort vibratory beam 34, thus changing the natural frequency thereof. The frequency signal produced at this time is processed to detect the value of the applied pressure.

The distortion sensitivity S of the vibratory transducer is expressed by the following $$S = \Delta f/fo = 0.118 \cdot (l/h)^2 \cdot \epsilon \quad (1)$$

wherein $\epsilon$ is the distortion.

Assuming that vibratory beam 34 has dimensions h=2 micrometers and l=200 micrometers, then $S=0.118 \cdot 10^4 \cdot \epsilon$. If $\epsilon=100$ ppm, then $\Delta f/fo=0.12$ (12%).

In the above embodiment, only one vibratory beam is formed in the vicinity of diaphragm 34. Where another vibratory beam is formed centrally in the diaphragm 34, the vibratory beams would be subjected respectively to compressive forces and tensile forces, making it possible to achieve a differential configuration. The output frequencies of the two vibratory beams are calculated to cancel out thermal distortions arising from temperature changes.

With the arrangement just described, since the vibratory beam is formed in vacuum in the pressure detecting diaphragm, a vibratory sensor of a simple construction can be produced which can generate a frequency signal and is of high Q and high stability.

Figure 8:
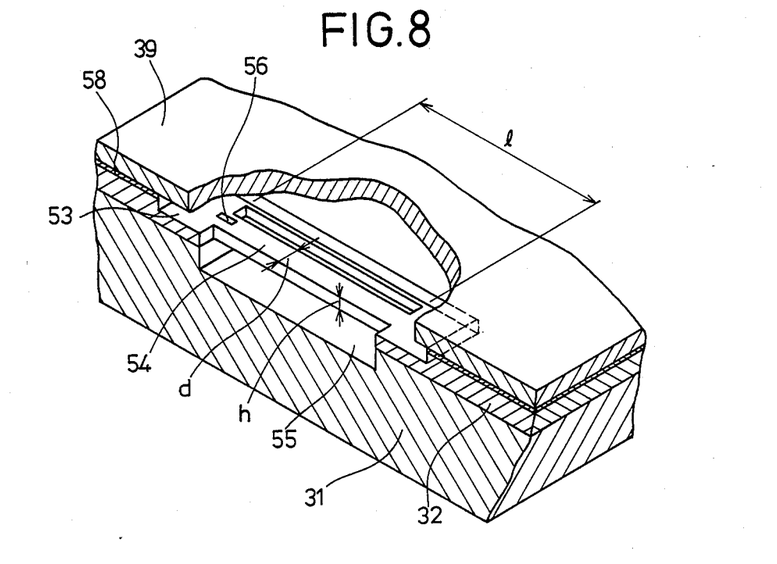
FIG. 8 is an enlarged perspective view, partly cut away, depicting a second illustrative embodiment of the invention, wherein the portion shown corresponds to portion A of FIG. 4.

FIG. 8 shows vibratory transducer according to a second illustrative embodiment wherein a portion is shown which corresponds to portion A of FIG. 4. A diaphragm 31 has an impurity diffused layer 32 formed in a substrate 30 which is identical to that of the first illustrative embodiment, the impurity diffused layer 32 having an impurity density identical to that of the first illustrative embodiment. Diffused layer 32 is locally etched to a certain depth to form a first hole 53. Then, the n+ diffused layer in the first hole 53 is etched to form slots, and the p layer of diaphragm 31 is underetched to form a second hole 55, thus forming a vibratory beam 54 supported at opposite ends and composed of an n+ layer. Vibratory beam 54 has the following dimensions, for example. Thickness h is 2 micrometers. Length l is 200 micrometers. Width d is 5 micrometers.

A p+ layer 56 is formed by diffusion in a portion of vibratory beam 54 whereat vibratory distortion is caused. A lead (not shown) extends from p+ layer 56 to an external circuit in insulated relation to the p layer of diaphragm 31. A silicon cover 39 is made of the same material as diaphragm 31. Silicon cover 39 and diaphragm 31 are connected by anodic joining in vacuum to evacuate first hole 53 and second hole 55. An SiO$_2$ layer 58, for example, serves as a joining and insulating member.

Figure 9:
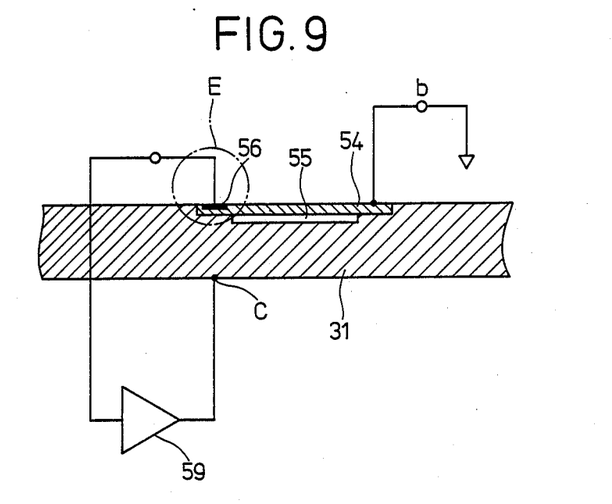
FIG. 9 is a schematic diagram depicting an electrical circuit connected to the embodiment of FIG. 8.

FIG. 9 shows the transducer having upper silicon cover 39 removed and also shows an electrical circuit connected to the transducer. When a bias voltage, which is positive with respect to diaphragm 31, is applied to n+ diffused layer 32 on diaphragm 31, p-type diaphragm 31 and vibratory beam 54 are insulated from each other. By adding an AC voltage to the bias voltage, an alternating electrostatic force can be applied to the vibratory beam 54. At the same time, a constant bias voltage is applied to p+ diffused layer 56 on one end of vibratory beam 54 while vibratory beam 54 is connected to a common potential, whereupon a diode current flows from the p+ diffused layer 56 to vibratory beam 54. This diode current varies at all times dependent on distortion applied to the diode. By feeding the diode current through a positive feedback loop to an external amplifier 59 vibratory beam 54 resonates at its natural frequency.

Figure 10:
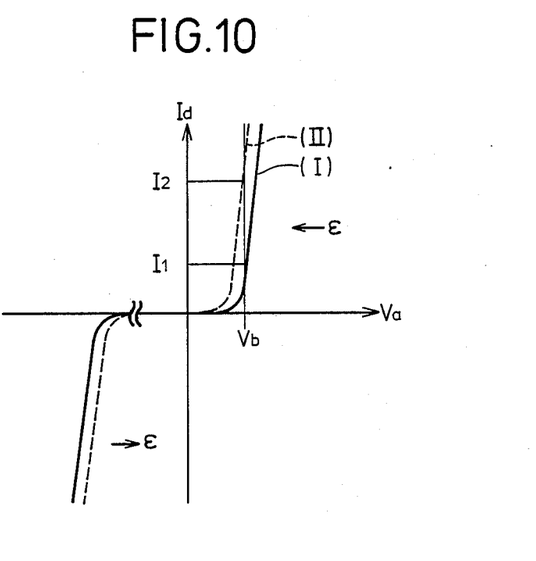
FIG. 10 is a graph depicting the relationship between current and voltage when a vibratory beam in a diode E of FIG. 9 is distorted.

FIG. 10 shows a graph depicting current flowing through a portion forming a diode E (shown enclosed by dot-dash line in FIG. 9) with the current being indicated on the vertical axis, and a voltage indicated on the horizontal axis By applying distortion $\epsilon$, V/I characteristic curve I (indicated by solid line) is shifted to V/I characteristic II (indicated by dotted line), and the current at the voltage Vb is avaried from $I_1$ to $I_2$. FIG. 10 indicates that the current varies due to distortion $\epsilon$ even if a reverse bias is applied.

The natural frequency of vibratory beam 54 varies with the force applied to diaphragm 31. Distortion sensitivity S can be expressed by equation (1) set forth hereinabove with reference to FIG. 4.

A distortion dependent change in the vibration frequency of vibratory beam 54 may be detected by a known vibration detecting device (not shown).

With the vibratory transducer of the second illustrative embodiment of FIG. 8, since the vibratory beam is formed in vacuum in the pressure detecting diaphragm, ideal elasticity characteristics can be attained, and a monolithic sensor which is of high Q and high stability can be produced.

Figure 11:
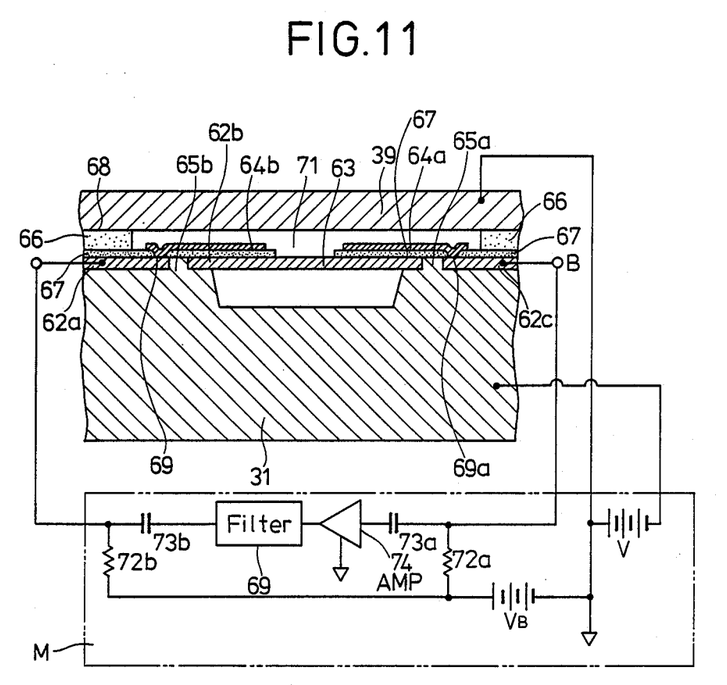
FIG. 11 is an enlarged cross sectional view depicting a third illustrative embodiment of the invention, wherein the portion shown corresponds to portion A of FIG. 4

FIG. 11 shows a third illustrative embodiment of the invention, wherein a diaphragm 31 has n+ layers 62a, 62b, 62c, formed locally in a substrate 30, that is identical to that of the first illustrative embodiment of FIG. 4, by diffusing impurities at a density ranging from $10^{17}$ to $10^{18}$ atoms/cm$^3$. A small vibratory beam 63, with opposite ends fixed, is formed by underetching diaphragm 31 below n+ layer 62b, except for opposite ends thereof. An SiO$_2$ layer 67 is formed exposing a substantially central portion of vibratory beam 63. SiO$_2$ layer 67 covers p layers 65a, 65b, exposed between the n+ layers 62a, 62c, except for small portions 69a, 69b thereon. Metal electrodes 64a, 64b, made for example of Au, are formed on SiO$_1$ layers and are connected to n+ layers 69a, 69b, exposed in SiO$_2$ layer 63. A glass layer 66 is formed above SiO$_2$ layer 67, except for an area above the vibratory beam 63, which unformed area forms a recess 71 opening above the vibratory beam 63. A silicon cover 39 is formed of the same material as that of diaphragm 31 and is connected to glass layer 66 by anodic joining.

Metal electrodes 64a, 64b disposed over vibratory beam 63 and silicon cover 39 disposed confronting metal electrodes 64a, 64b, across recess 71 jointly constitute a capacitor.

An oscillator circuit M (which is shown as beint enclosed by two-dot-dash line) is constructed as an external circuit or on the silicon substrate The oscillator circuit applies a DC bias voltage VB between silicon cover 39 and metal electrodes 64a, 64b via resistors 72a, 72b, and metal electrodes 64a, 64b are AC coupled through capacitors 73a, 73b, filter 69 and amplifier 74.

The vibratory transducer of the above arrangement constitutes a positive feedback circuit by suitably selecting the phases of the gains of amplifier 74 and filter 69 so that vibratory beam 63 can be oscillated at a natural frequency.

Figure 12:
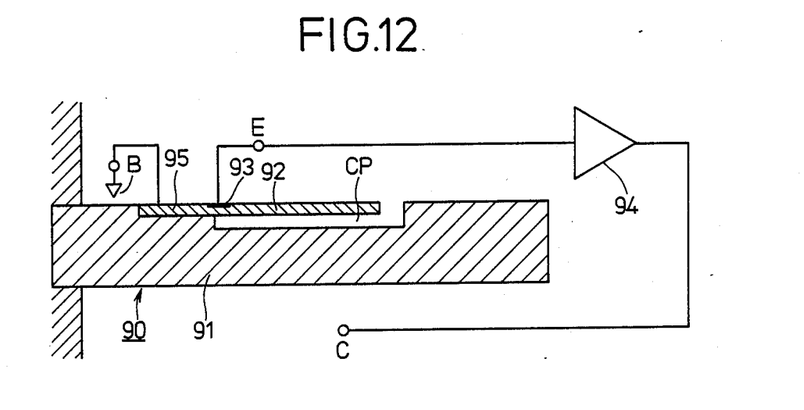
FIG. 12 is a cross sectional view depicting a fourth illustrative embodiment of the invention, wherein the embodiment is illustratively used as a cantilever type arrangement.

FIG. 12 illustrates a fourth illustrative embodiment of the invention, wherein a vibratory transducer 90 is used as a cantilever. A diffused layer 95 is formed in a silicon substrate 91 identical to that of the first illustrative embodiment of FIG. 4, and a cantilevered vibratory beam 92 is formed by underetching except for one end of the diffused layer 95. A p-type diffused layer 93 is formed on the end of the diffused layer 95.

The p-type silicon substrate 91, the n-type cantilevered vibratory beam 92, and the p-type diffused layer 93 jointly constitute a pnp transistor By connecting an emitter grounded amplifier 64 between the silicon substrate 91 and the cantilevered vibratory beam 92, the pnp transistor constitutes a self excited oscillator circuit.

Figure 13:
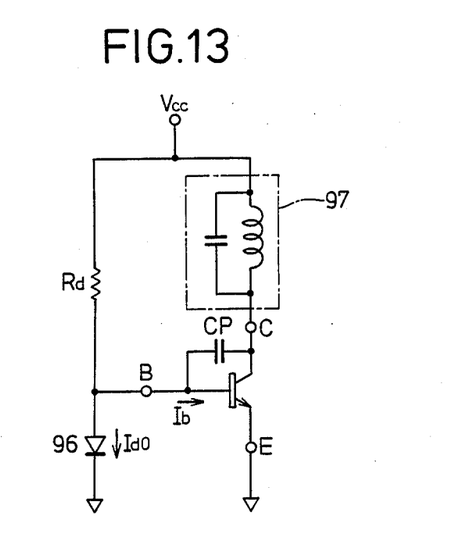
FIG. 13 is a circuit diagram depicting an oscillating circuit for the embodiment of FIG. 12.

FIG. 13 illustrates an oscillator circuit for the vibratory transducer shown in FIG. 12. The oscillator circuit comprises a reference diode 96 for supply a constant current, there being an electrostatic capacity CP formed between cantilevered vibratory beam 92 and silicon substrate 91 shown in FIG. 12. The oscillator circuit is self oscillated by applying a voltage Vcc to silicon substrate 91 serving as a collector through an LC circuit 97.

Since oscillator circuit is constructed of the diode and transistor formed on silicon substrate 91, the vibratory transducer is advantageously small in size and stable in performance.

Figure 14:
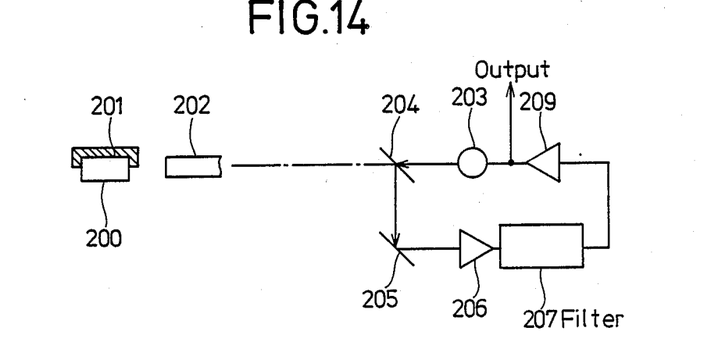
FIG. 14 is a diagram depicting a fifth illustrative embodiment of the invention.

FIG. 14 shows a fifth illustrative embodiment of the invention wherein a pyroelectric member is fixed to a vibratory beam manufactured in the same manner as that of the first illustrative embodiment of FIG. 4. Upon exposure to light, the pyroelectric member is subjected to electrostriction to distort the vibratory beam to enable the same to be self oscillated. The arrangement comprises a vibratory beam 200, a pyroelectric member 201, such as made of PZT or ZnO, optical fiber 202, an LED 203, and a half silvered mirror 204. Light emitted from LED 203 passes through half silvered mirror 204 and optical fiber 202 and is applied to pyroelectric member 201 which generates pyroelectricity. As pyroelectric member 201 is subjected to electrostriction, vibratory beam 200 is distored and hence displaced, whereupon the amount of light applied to pyroelectric member 201 is varied to cause vibratory beam 200 to be self oscillated. The frequency of vibration of vibratory beam 200 varies with the force applied to the diaphragm (not shown). Such a frequency change is fed back through optical fiber 202, half silvered mirror 204, mirror 205, amplifier 203, filter 207, and amplifier 209 to LED 203. By picking up the vibration frequency from a point between emaplifier 209 and LED 203, the force applied to the diaphragm can be detected and outputted as an output signal.

Figure 15:
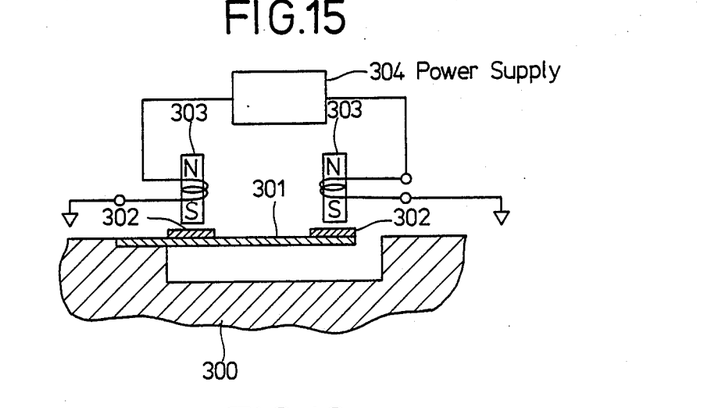
FIG. 15 is a cross sectional view depicting a sixth illustrative embodiment of the invention.

FIG. 15 shows a sixth illustrative embodiment of the invention, wherein magnetic members 302, made, for example of Ni, are attached, respectively, to the opposite ends of a vibratory beam 301 formed on a p-type silicon substrate 300 in the same manner as that of the first illustrative embodiment of FIG. 4. Electromagnets 303 are disposed in the vicinity of magnetic members 302. Vibratory beam 301 is vibrated at a natural frequency by passing an alternating current from a power supply 304 through electromagnets 303.

Figure 16:
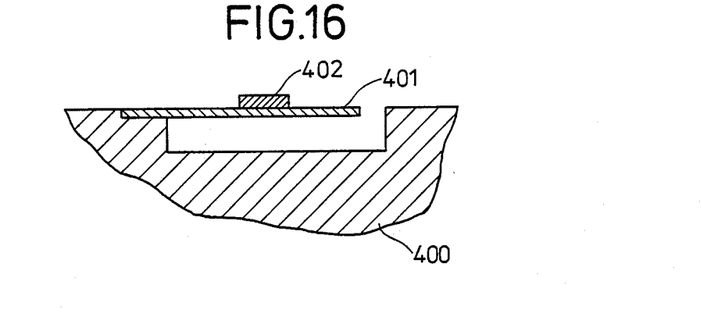
FIG. 16 is a cross sectional view depicting a seventh illustrative embodiment of the invention.

FIG. 16 illustrates a seventh illustrative embodiment of the invention. This embodiment is designed to prevent a zero point from being varied due to changes in the vibration frequency which would arise from variation in the density around a vibratory beam 401 formed on a silicon substrate 400 in the same manner as that of the first illustrative embodiment of FIG. 4. A member 402, made for example of Au, and having a large density is fixed to a vibration peak portion vibratory beam 401 to lower the sensitivity to density variations.

Figure 17A:
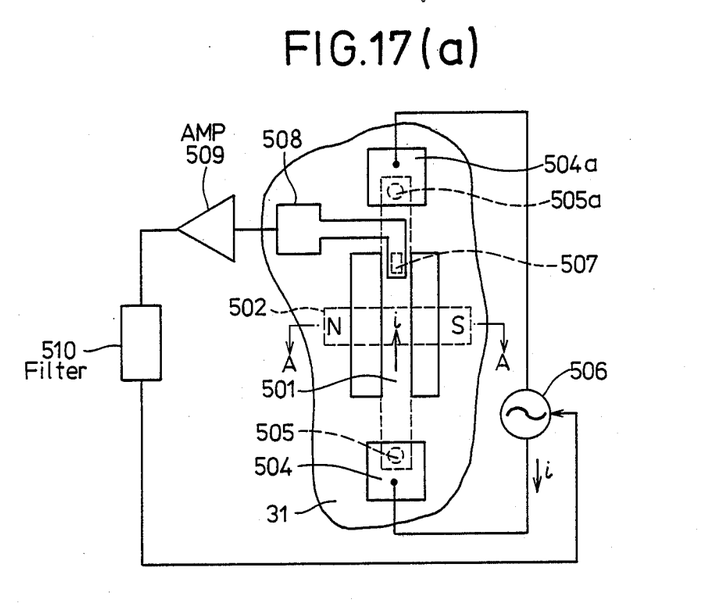
FIGS. 17(A) and 17(B) are diagrams depicting an eighth illustrative embodiment of the invention.
Figure 17B:
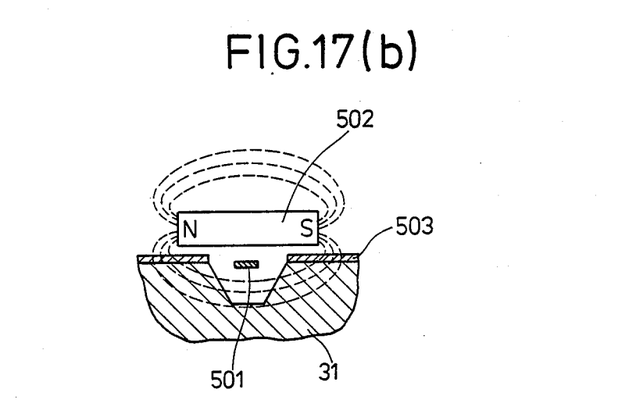

FIGS. 17(A) and 17(B) illustrate an eighth illustrative embodiment of the invention with FIG. 17(A) being an enlarged fragmentary plan view of a diaphragm on which a vibratory beam 501 is formed in the same manner as that of the fist embodiment, and with FIG. 17(B) being a cross sectional view taken along line A—A of FIG. 17(A). A DC magnetic field is applied in a direction normal to the direction in which the vibratory beam 501 vibrates, and vibratory beam 501 is vibrated by passing an alternating current through vibratory beam 501.

Disclosed is a p-type silicon substrate 31 on which the diaphragm is formed, an n-type vibratory beam 501 formed by underetching, a magnet 502 disposed above vibratory beam 501 and extending substantially centrally across vibratory beam 501, and an SiO$_2$ film 503 serving as an insulating film. Metal electrodes 504,504a, for example made of Au, have ends connected by contact holes 505,505a, in SiO$_2$ layer 503 to an n+ layer extending from vibratory beam 501 and opposite ends connected by leads to a current supply 506. A piezoelectric element 507, made for example of ZnO, is disposed near the supported portion of vibratory beam 501, and is covered with a metal electrode 508. Connected to the metal electrode 508 is amplifier 509 and filter 510. Although not shown, a reverse voltage is applied between vibratory beam 501 and silicon substrate 31 to insulate them from each other.

When an alternating current i is passed from current supply 506 via metal electrodes 504,504a, through vibratory beam 501, vibratory beam 501 is deformed under a force applied in a direction normal to the directions of the magnetic field and the current. Upon deformation of vibratory beam 501, the amount of charge on piezoelectric element 507 is varied as a function of the extent to which vibratory beam 501 is deformed, and is detected through metal electrodes 508 connected to piezoelectric element 407. The detected signal is amplified by amplifier 509 and is fed through a positive feedback loop via filter 510 back to current supply 506. Therefore, the system is self oscillated at a natural frequency thereof.

Figure 18:
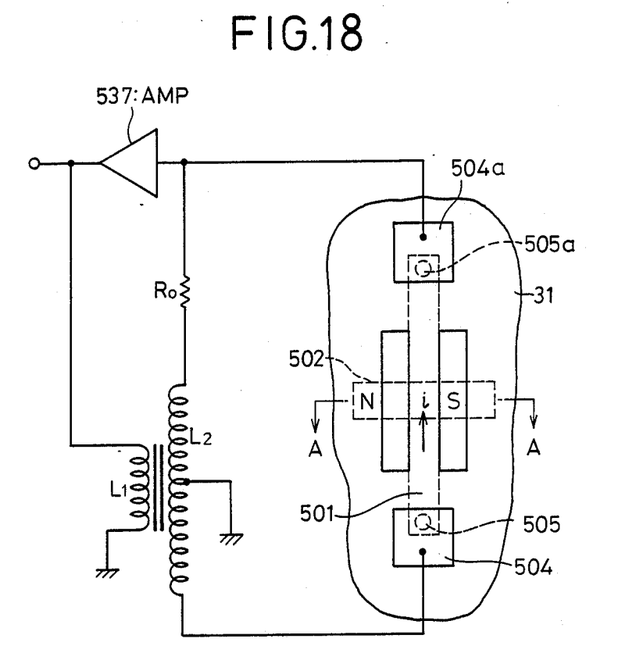
FIG. 18 is a plan view depicting a ninth illustrative embodiment of the invention, wherein the shown portion corresponds to portion A of FIG. 4, and wherein an electrical circuit is also shown connected to the embodiment.
Figures 19A, 19B:
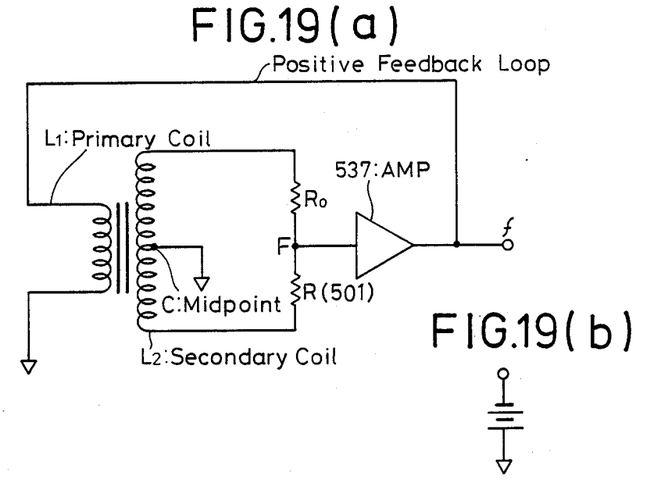
FIGS. 19(A) and 19(B) are circuit diagrams of the arrangement of FIG. 18.

FIGS. 18,19(A) and 19(B) show a ninth illustrative embodiment of the invention with FIG. 18 being an enlarged fragmentary plan diagram wherein a vibratory beam is formed in the same manner as that of the first illustrative embodiment of FIG. 4, and an electrical circuit is connected to the vibratory beam, and with FIGS. 19(A) and 19(B) being electrical diagrams of the FIG. 18 arrangement, and showing a power supply for applying a reverse bias voltage between a p-type layer and an n+ type layer.

In FIG. 18 there is disclosed a silicon substrate 31, a vibratory beam 501, a magnet 502 disposed above and extending substantially centrally across vibratory beam 501, and metal electrodes 504,504a, made for example of Al. Metal electrode 504a has an end connected to one end of vibratory beam 501 through a contact hole 505a defined in an SiO$_2$ layer extending from vibratory beam 501 and an opposite end coupled via a lead to one terminal of a comparison resistor Ro having substantially the same resistance as that of vibratory beam 501 and a terminal of an amplifier 537. Amplifier 537 has an output terminal for issuing an output signal, the output terminal being connected to one end of a primary coil L1, the other end of which is coupled to common.

The other terminal of the comparison resistor Ro is connected to one end of a secondary coil L2 with its intermediate tap connected to common. The other end of the secondary coil L2 is connected to metal electrode 504a formed on the other end of vibratory beam 501.

A reverse bias voltage is applied between the p type layer (substrate 31) and the n+ type layer (vibratory beam 501) to insulate them, and an alternating current i is passed through vibratory beam 501. The impedance of the vibratory beam is increased by electromagnetic induction at the resonant frequency of vibratory beam 501, so that an unbalanced signal is produced at the n+ layer by a bridge comprising comparison resistor Ro and secondary coil L2 with its intermediate tap connected to common. The unbalanced signal is then amplified by amplifier 537 and fed through a positive feedback loop to primary coil L1 to thereby enable the system to be self oscillated at the natural frequency of the vibratory beam.

The impedance R of vibratory beam 501 increases with the natural frequency thereof The impedance R is expressed as follows.

$$R \approx (1/2 2 2) \cdot (1/\sqrt{Eg} \; 2) \cdot (AB^2 l^2 / bh^2) \cdot Q + Ro$$

wherein E is modulus of elasticity; g is gravitational acceleration; $\gamma$ is the density of a material that the vibratory beam is made of; A is constant determined by vibration mode B is flux density; l is length of the vibratory beam; b is width of the vibratory beam; h is thickness of the vibratory beam; Q is sharpness of resonance; Ro is DC resistance value.

Since Q of the vibratory beam has a value ranging from several hundreds to several tens of thousands in the above equation, a large amplitude signal can be produced as an output from the amplifier under the resonant condition. With the gain of the amplifier being selected to be sufficiently high for positive feedback, the system is self oscillated at the natural frequency. According to the above embodiment, the vibratory transducer uses coils as oscillating means and has the following advantages over the capacitive type vibratory transducer.

(1) The vibratory beam has a low impedance and can be easily vibrated.

(2) The vibratory beam can easily be vibrated even if it is small in size.

(3) No electrical discharge is caused since the operating voltage is low.

(4) The vibratory beam vibrates stably since no excessive tension is applied thereto.

Figure 20:
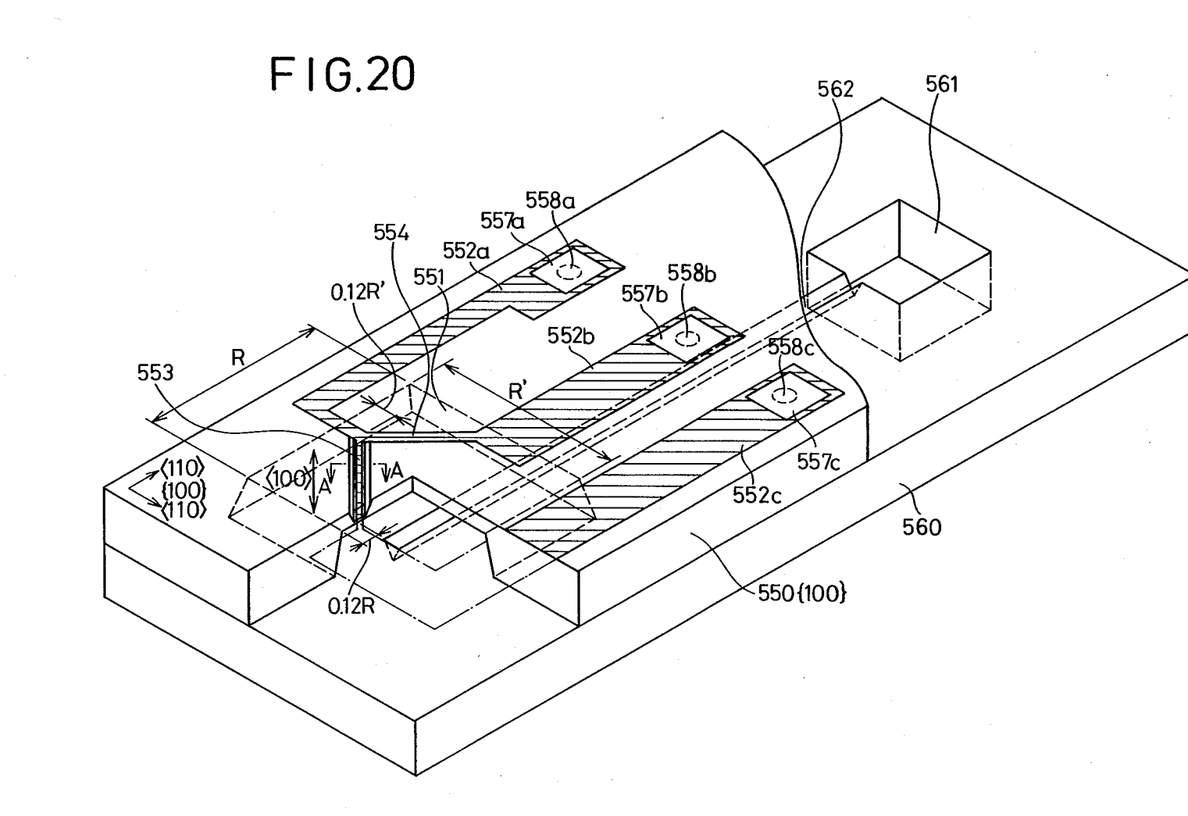
FIG. 20 is a perspective view depicting a tenth illustrative embodiment of the invention.

FIG. 20 is a fragmentary perspective view, partly in cross section, of a vibratory beam according to a tenth illustrative embodiment of the invention, wherein the vibratory beam uses a silicon substrate as with the first embodiment of FIG. 4. The depicted electrical circuit is used to vibrate the vibratory beam and is the same as that of FIGS. 19(A),19(B). The surface of silicon substrate 550 is the crystalline face which is indicated by (100). One face of the silicon substrate 550 is etched to form a rectangular diaphragm 551 having a side in the <110> direction. Another face (not etched) including the diaphragm 551 has n+ diffused layers 552a, 552b, 552c formed thereon by adding impurities at a density ranging from $10^{17}$ to $10^{18}$ atoms/cm$^3$. A vibratory beam 553 having a longitudinal axis extending in the <100< direction is formed on the n+ diffused layer on diaphragm 551. Vibratory beam 553 is formed by photolithography and selective etching on the n+ and p layers on diaphragm 551. The cross sectional shape taken along line A—A is the same as shown in FIG. 17(B). Vibratory beam 553 is disposed at a position which is spaced from an adjacent side of diaphragm 551 by about 0.12 times the length of one side of the diaphragm. A comparison resistor 554 is composed of an n+ diffused layer and is disposed on diaphragm 551 in contact with one end of vibratory beam 553 in symmetrical configuration. Comparison resistor 554 has the same resistance as that of vibratory beam 553. Metal electrodes 557a, 557b, 557c, made for example of Al, are connected to the n+ diffused layers 552a, 552b, 552c, extending from vibratory beam 553 through contact holes 558a, 558b, 558c, defined in an SiO$_2$ layer 503 (see FIG. 17(B)). A base 560 has a pressure introducing hole 561 and a pressure introducing groove 562, the pressure introducing groove 562 interconnecting the pressure introducing hole 561 and a hole for forming the diaphragm 551 and being hermetically fixed.

The inventors have calculated, using the finite element method and confirming the results experimentally, that when a pressure P is applied to a square diaphragm having a side R, the surface of the diaphragm is subjected to a maximum surface displacement at a point spaced 0.12R from an end of an adjacent side. In this embodiment, since vibratory beam 553 is formed in this position, a maximum degree of distortion can be obtained for the vibratory beam.

The distortion applied to the vibratory beam is expressed by the following equation.

$$\epsilon \approx 0.1 \; (1/E)\cdot(a/h)^2 \cdot P$$

wherein E is Young's modulus; a is length of one side of the square diaphragm; h is the thickness of the diaphragm and P is the pressure.

The natural frequency (lowest order mode) of the vibratory beam is expressed by the following equation.

$$f = fo(1+\alpha\epsilon)$$

$$\alpha = 0.118(l/t)^2$$

wherein l is length of the vibratory beam; t is thickness of the vibratory beam; and fo is natural frequency when P=0.

The vibratory beam thus constructed can be self oscillated at the natural frequency by being vibrated by the electric circuit arranged as shown in FIGS. 19(A) and 19(B).

The frequency of vibration of each of the transducers according to the first through tenth illustrative embodiments varies dependent on the temperature coefficient of the modulus of elasticity of silicon. Thus, these transducers can be housed in a vacuum container and used as a thermometer. In such an application, the frequency of vibration of the vibratory transducer is given by the following equation.

$$f^2 = fo^2(1+\gamma\Delta T)$$

wherein fo is the natural frequency at the reference temperature; $\gamma$ is the temperature coefficient which is 106.8 ppm/K in the <100> direction; and $\Delta T$ is the temperature difference with the reference temperature.

The vibratory transducer can also be used as a densimeter. In such an application, the frequency of vibration of the vibratory transducer is given by the following equation.

$$f^2 = fo^2(1+\beta\rho)^{-1}$$

wherein fo is the natural frequency in vacuum; $\beta$ is the fluid density sensitivity; and $\rho$ is fluid density.

The preferred methods of etching a silicon substrate according to the invention will now be described with reference to FIGS. 21,22,23,24. The invention is concerned with a method for selectively etching a semiconductor silicon wafer, and a method for etching either one of two silicon wafers which are connected together by a pn junction.

The following method of finely etching a single silicon crystal is described, for example, in IEEE, Electron Device Letters, Vol. ed1, 2, No. 2, February 1981, pages 44,45; and comprises the steps of placing a platinum (Pt) electrode in an alkaline aqueous solution of ethylene diamine pyrocatechol (EDP) or a potassium hydroxide (KOH), and selectively etching by applying a voltage in the range of from +0.5 to 0.6 volt to either a p-type or n-type of silicon. This prior art method was found to be unsatisfactory after various tests conducted by the inventors. Some of the disadvantages and deficiencies of the prior art method are as follows.

(1) The etching process is unstable because it is not stopped at the voltage range of 0.5 to 0.6 volt, dependent on the density of impurities in silicon.

(2) If the resistivity of the n layer is high, the current flow is rendered poor at a position spaced from the location connected to the lead, and is not brought into the passive state, thus causing the layer to be locally etched.

Our inventive methods aim to overcome these and other deficiencies and disadvantages of the prior art methods.

Figure 21:
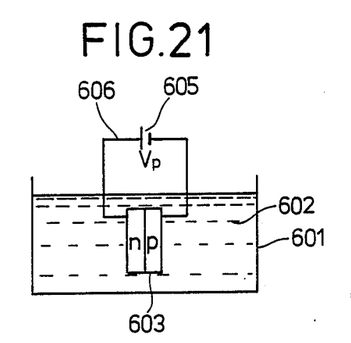
FIG. 21 is a cross sectional view depicting a bath and electrical circuit arrangement used in the process of etching a silicon substrate.

FIG. 21 depicts a bath and electrical connections used to carry out a silicon etching method according to the invention, wherein a container 601 contains an alkaline solution (such as potassium hydroxide) 602. A combination 603 of a p type silicon substrate and an n type silicon formed thereon by epitaxial growth is placed in solution 602. A DC power supply 605 from which a positive voltage is applied via lead 606 to the n type layer and a negative voltage is applied via lead 606 to the p type layer.

With this arrangement, a reverse bias is applied between the n type and p type silicon layers. Under the voltage applied from power supply 605 to the n type layer, a current flow through the alkaline solution 602 to the p type layer. As a result, an insoluble film is formed on the surface of the n type layer, bringing the layer into the passive state After the process of bringing the layer into the passive state is finished, the current is greatly reduced. Thus, the rate of etching the n type layer with the alkaline solution is lowered. As a result, since the etching rates of the n type layer and p type layer are widely different (for example, 1/300), the silicon substrate is selectively etched According to this process, by using the n layer of the pn junction silicon substrate as an anode and the p layer thereof as a cathode, an anode current flows into the alkaline solution only from the n layer, but never from the p layer. Because the passive state is created only by the anode current, the n layer, serving as the anode, can be stably brought into the passive state.

Where a p layer of a small area is exposed on the surface of the n layer and only that player is to be etched, the player may not necessarily be etched if the area df the player to be etched is small (for example 0.1 mm$^2$). This shortcoming is believed to result from the fact that a barrier is developed to prevent the flow of ions by the applying of a positive DC voltage to the n layer.

Figure 22:
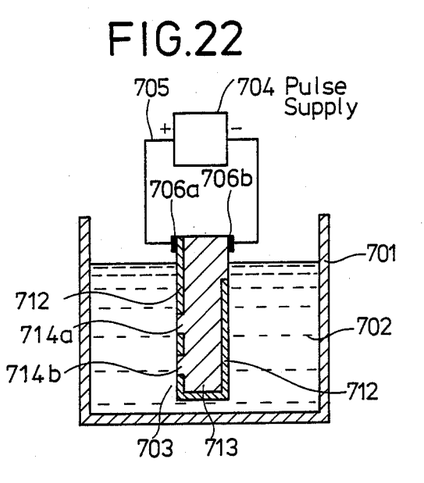
FIG. 22 is a cross sectional view depicting another bath and electrical circuit arrangement used in the process of etching a silicon substrate.

FIG. 22 depicts a bath and electrical connections used to carry out another silicon etching method , wherein a silicon substrate having a pn junction is immersed in an alkaline solution, and a pulsed voltage is repeatedly applied between the p and n layers of the silicon substrate, or the silicon substrate and the alkaline solution.

Figure 23:
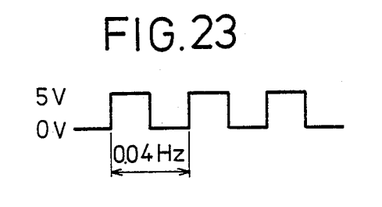
FIG. 23 is a diagram depicting the waveform of a pulsed voltage which is applied in the process depicted in FIGS. 22,24.

In FIG. 22 a container 701 contains an alkaline solution (such as for example potassium hydroxide (KOH 4N 80° C.)702. A silicon substrate 703 composed of a p layer 713 covered with an n layer (except for small areas 714a, 714b) is in the solution 702 as depicted. A pulse power supply 704 is connected via lead 705 to electrode 706a formed on an end of n layer 712, and to electrode 706b formed on an end of p layer 713. The silicon substrate 703 is immersed in the alkaline solution 702, except for electrodes 706a, 706b. A pulsed voltage of rectangular waveform, such as shown in FIG. 23, is applied from power supply 704 between electrodes 706a, 706b. The voltage preferably has a peak value of 5 volts and a repetition period of 0.04 Hz. The n layer 712 is formed in covering relation to substantially the entire surface of the player 713, except that small areas of p layers 714a, 714b, are exposed These exposed areas 714a, 714b may have a width of 10 micrometers and a length of 100 micrometers, for example.

The voltage, of 5 volts, is applied from the pulse power supply 704 to the n layer 712 at a period of 0.04 Hz. As long as the voltage of 5 volts is impressed, an insoluble film is formed on the surface of the n layer 712. When the voltage is not applied, the formed insoluble film starts being etched by the alkaline solution. Before the n layer 712 is exposed, however, the voltage is applied again to maintain the insoluble film. When the voltage applied to the n layer 712 is 5 volts, there is a barrier on the small exposed areas 714a, 714b of the p layer 713, thus preventing ions from flowing. When the voltage applied to the n layer 712 is zero, however, no barrier exists and hence the ions are allowed to flow freely, thus etching the player 712 even in the small exposed areas. The etching rate of the small areas 714a, 714b of the p layer 712 under the above conditions is about 1.2 micrometers/min.

While in the above embodiment specific numerical values are given for the areas 714a, 714b of p layer 712, the kind and temperature of the alkaline solution 702, and the pulsed voltage, the etching rate varies dependent on the density and temperature of the alkaline solution. Thus, the invention is not limited to the above numerical values.

Figure 24:
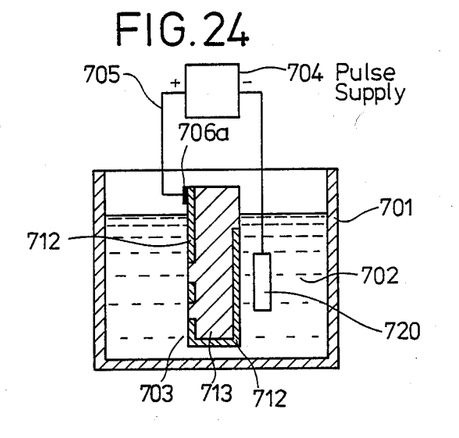
FIG. 24 is a cross sectional view depicting a bath and electrical circuit arrangement used in a modified process for etching a silicon substrate.

FIG. 24 shows a modification of the embodiment of FIG. 22. Those parts depicted in FIG. 24 which are identical to those of FIG. 22 are denoted by identical reference characters, and will not be further described hereat for sake of clarity. In the modification, the lead (unnumbered) from the negative (−) terminal of the Pulse power supply 704 is not connected to the player 713 (as in FIG. 22), but, instead, is connected to a separate platinum electrode 720 immersed in the alkaline solution 702.

According to the embodiments shown in FIG. 22,24, small areas of the silicon substrates can easily be etched, and the illustrated arrangements can also be used as a testing device for ascertaining conductivity types when the conductivity type of a layer formed on a silicon substrate is not known.

With the invention, since a vibratory beam of an n type layer is formed on a single silicon crystal, it can be etched irrespective of the density of impurities added thereto. Thus, a diode and a transistor, including the vibratory bean, can be formed in a vibratory transducer, so that means for vibrating and detecting vibrations of the vibratory beam can easily be provided. The vibratory beam can also be finely etched.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. A vibratory transducer for vibrating a vibratory beam formed on a single silicon crystal at a natural frequency thereof and for detecting a change in the frequency of vibration of the vibratory beam dependent on change in a force applied on said single silicon crystal or environment, said transducer comprising a single silicon crystal which comprises a p-type semiconductor conductor containing impurities at a concentration of 10 or 10$^{17}$ atoms/cm$^3$ or less, and an n+ diffused layer of a single silicon crystal containing impurities at a concentration ranging from 10$^{17}$ to 10$^{18}$ atoms/cm$^3$; a vibratory beam formed of the n+ diffused layer by under-etching said n+ diffused layer by the selective etching technique; said vibratory beam having at least one fixed point; means for causing said vibratory beam to vibrate at the natural frequency; and detecting means for detecting the vibration.

2. The transducer of claim 1, further comprising a diaphragm with a hole being formed in a surface of said diaphragm, said hole having one end closed and another end open, wherein said vibratory beam is formed in said hole.

3. The transducer of claim 2, wherein said surface of said diaphragm is covered with another member to keep an area surrounding said vibratory beam under vacuum.

4. The transducer of claim 3, further comprising two electrodes and a piezoelectric material sandwiched between said two electrodes and attached to a portion of said vibratory beam to enable distortion, said vibratory beam being vibrated at the natural frequency thereof by applying an AC voltage between said two electrodes.

5. The transducer of claim 3, further comprising two electrodes and a piezoelectric material sandwiched between said two electrodes and attached to a portion of said vibratory beam to enable distortion, so that the amount of charge generated between said electrodes is detected.

6. The transducer of claim 3, wherein comprising means for applying a voltage which is a combination of a DC reverse bias voltage and an AC voltage having the natural frequency of said vibratory beam between said vibratory beam and a p layer which is not vibrated, to thereby vibrate said vibratory beam at said natural frequency.

7. The transducer of claim 3, wherein a pn junction is formed by diffusing impurities locally in an area of said vibratory beam which is subjected to vibratory distortion, and further comprising means for supplying a current to said pn junction to keep the potential of the junction at a constant value, means for amplifying change in said current caused by said vibratory distortion and for applying the amplified change in current to means for vibrating said vibrating means, wherein said means for supplying, means for amplifying and applying define a positive feedback circuit for vibrating said vibratory beam at the natural frequency.

8. The transducer of claim 3, wherein a p layer is formed by diffusing impurities locally in an area of said vibratory beam which is subjected to vibratory distortion, so that the vibratory distortion is detected by a piezoelectric effect of said player.

9. The transducer of claim 3, wherein a pyroelectric material is attached to a vibration node portion of said vibratory beam so that said vibratory beam is vibrated at the natural frequency by applying light to said pyroelectric material.

10. The transducer of claim 3, wherein a material of a large density is attached to a vibration peak portion of said vibratory beam, thereby lowering the sensitivity to change in density of fluid around said vibratory beam.

11. The transducer of claim 3, wherein means applies a DC magnetic field in a direction normal to the direction of vibration of said vibratory beam, so that said vibratory beam is vibrated at the natural frequency by supplying an alternating current to said vibratory beam.

12. The transducer of claim 3, wherein means provides a DC magnetic field in a direction normal to the longitudinal direction of said vibratory beam, said means comprising a magnetic circuit disposed closely to the vibratory beam, two primary and secondary coils magnetically coupled to each other, said secondary coil having an intermediate tap connected to common, a comparison resistor having substantially the same resistance as that of said vibratory beam and being connected to said secondary coil in series with said vibratory beam, a junction between said comparison resistor and said vibratory beam being connected to an input terminal of an amplifier, said amplifier having suitable gain and being connected to said primary coil, wherein said means define a positive feedback oscillation circuit which is self oscillated at the natural frequency of said vibratory beam.

13. The transducer of claim 3, wherein said n-type layer is formed by adding impurities locally to the surface of a p-type silicon substrate having a (100) face, said silicon substrate being underetched by selective etching to form said vibratory beam which has opposite ends fixed and a longitudinal 100 direction, the reverse(100) face of the silicon substrate in which said vibratory beam is formed being etched to form a rectangular diaphragm having one side in a <110> direction, and further comprising means for applying a DC magnetic field in a direction normal to said vibratory beam and means for passing a current through said vibratory beam, said opposite ends of said vibratory beam being located at a position which is spaced from an adjacent side of said diaphragm by a distance about 0.12 times the length of one side of said diaphragm, and further comprising a comparison resistor held on said diaphragm in contact with one end of said vibratory beam in symmetrical configuration and having the same resistance as that of said vibratory beam.

14. The transducer of claim 1, wherein said vibratory beam is formed in an alkalene aqueous solution while applying a negative DC or pulsed voltage to a p-type layer and a positive DC or pulsed voltage to an n+ layer.

15. The transducer of claim 1, further comprising two electrodes and a piezoelectric material sandwiched between said two electrodes and attached to a portion of said vibratory beam to enable distortion, said vibratory beam being vibrated at the natural frequency thereof by applying an AC voltage between said two electrodes.

16. The transducer of claim 1, further comprising two electrodes and a piezoelectric material sandwiched between said two electrodes and attached to a portion of said vibratory beam to enable distortion, so that the amount of charge generated between said electrodes is detected.

17. The transducer of claim 1, wherein comprising means for applying a voltage which is a combination of a DC reverse bias voltage and an AC voltage having the natural frequency of said vibratory beam between said vibratory beam and a player which is not vibrated, to thereby vibrate said vibratory beam at said natural frequency.

18. The transducer of claim 1, wherein a pn junction is formed by diffusing impurities locally in an area of said vibratory beam which is subjected to vibratory distortion, and further comprising means for supplying a current to said pn junction to keep the potential of the junction at a constant value, means for amplifying change in said current caused by said vibratory distortion and for applying the amplified change in current to means for vibrating said vibrating beam, wherein said means for supplying, means for amplifying and applying define a positive feedback circuit for vibrating said vibratory beam at the natural frequency.

19. The transducer of claim 1, wherein a player is formed by diffusing impurities locally in an area of said vibratory beam which is subjected to vibratory distortion, so that the vibratory distortion is detected by a piezoelectric effect of said player.

20. The transducer of claim 1, wherein a pyroelectric material is attached to a vibration node portion of said vibratory beam, so that said vibratory beam is vibrated at the natural frequency by applying light to said pyroelectric material.

21. The transducer of claim 1, wherein a material of a large density is attached to a vibration peak portion of said vibratory beam, thereby lowering the sensitivity to change in density of fluid around said vibratory beam.

22. The transducer of claim 1, wherein means applies a DC magnetic field in a direction normal to the direction of vibration of said vibratory beam, so that said vibratory beam is vibrated at the natural frequency by supplying an alternating current to said vibratory beam.

23. The transducer of claim 1, wherein means provides a DC magnetic field in a direction normal to the longitudinal direction of said vibratory beam, said means comprising a magnetic circuit disposed closely to the vibratory beam, two primary and secondary coils magnetically coupled to each other, said secondary coil having an intermediate tap connected to common, a comparison resistor having substantially the same resistance as that of said vibratory beam and being connected to said secondary coil in series with said vibratory beam, a junction between said comparison resistor and said vibratory beam being connected to an input terminal of an amplifier, said amplifier having suitable gain and being connected to said primary coil, wherein said means define a positive feedback oscillation circuit which is self oscillated at the natural frequency of said vibratory beam.

24. The transducer of claim 1, wherein said n-type layer is formed by adding impurities locally to the surface of a p-type silicon substrate having a (100) face, said silicon substrate being underetched by selective etching to form said vibratory beam which has opposite ends fixed and a longitudinal $<100>$ direction, the reverse (100) face of the silicon substrate in which said vibratory beam is formed being etched to form a rectangular diaphragm having one side in a $<110>$ direction, and further comprising means for applying a DC magnetic field in a direction normal to said vibratory beam and means for passing a current through said vibratory beam, said opposite ends of said vibratory beam being located at a position which is spaced from an adjacent side of said diaphragm by a distance about 0.12 times the length of one side of said diaphragm, and further comprising a comparison resistor held on said diaphragm in contact with one end of said vibratory beam in symmetrical configuration and having the same resistance as that of said vibratory beam.

* * * * *